United States Patent [19]
Root et al.

[11] Patent Number: 5,516,564
[45] Date of Patent: May 14, 1996

[54] STERILE IRRADIATED HYDROPHOBIC PIPETTE TIP

[75] Inventors: David Root, Lexington, Mass.; Lewis Lawton, Ossippe, N.H.

[73] Assignee: Costar Corporation, Cambridge, Mass.

[21] Appl. No.: 54,442

[22] Filed: Apr. 28, 1993

[51] Int. Cl.$^6$ .......................... B29D 22/00; B32B 27/00; B65B 1/04; B65D 97/18
[52] U.S. Cl. .......................... 428/35.7; 141/18; 141/85; 222/420; 222/571; 422/100; 428/36.9; 428/36.92; 428/421
[58] Field of Search .............. 422/100, 99; 525/199; 428/35.7, 36.6, 36.7, 36.9, 36.92, 421; 604/27, 30, 35, 118, 313; 222/420, 571; 401/137; 141/18, 69, 85, 92

[56] References Cited

U.S. PATENT DOCUMENTS

| | | | |
|---|---|---|---|
| 4,563,104 | 1/1986 | Saint-Amand | 401/139 |
| 5,019,140 | 5/1991 | Bowser et al. | 55/159 |
| 5,032,641 | 7/1991 | Nanishi et al. | 524/544 |
| 5,075,378 | 12/1991 | Smierciak et al. | 525/109 |
| 5,250,589 | 10/1993 | Keating et al. | 523/206 |

FOREIGN PATENT DOCUMENTS

| | | |
|---|---|---|
| 0423179 | 4/1991 | European Pat. Off. . |
| 207154 | 2/1984 | Germany . |
| 250661A1 | 10/1987 | Germany . |
| 1279663A1 | 12/1986 | U.S.S.R. . |
| 910513 | 4/1991 | WIPO . |

Primary Examiner—Paul J. Thibodeau
Assistant Examiner—Stephen Sand
Attorney, Agent, or Firm—Wolf, Greenfield & Sacks

[57] ABSTRACT

The present invention features hydrophobic articles of manufacture having a composition comprising a plastic and a fluoropolymer. The plastic-fluoropolymer composition is resistant to irradiation allowing the article to maintain hydrophobic properties through standard irradiation processes.

2 Claims, 3 Drawing Sheets

STERILE IRRADIATED HYDROPHOBIC PIPETTE TIP

INTRODUCTION

This invention relates generally to hydrophobic articles of manufacture useful for transporting dispensing, containing or probing liquids. In particular, the invention relates to the hydrophobic articles of manufacture comprising a mixture of molded plastic which plastic is capable of maintaining its hydrophobicity following irradiation.

BACKGROUND OF THE INVENTION

The accuracy in which liquids can be dispensed influences the precision of scientific instruments and manual operations. Devices for dispensing liquids include pipettes, capillary tubes, droppers, air and positive displacement pipettes and syringes. These devices can be operated manually or can be incorporated into larger instrumentation.

Hydrophobicity plays an important role in the accuracy of liquid dispensing devices. As used herein the term "hydrophobic" is used in the sense of repelling water. The term "hydrophilic" is used in an opposite sense, namely, attracting water.

One source of error arising in devices which dispense liquids is the adherence of liquid to the housing of such device. In the case of a pipette, fluid may cling to the inside or outside of the tip. Such fluid does not release uniformly from the orifice, altering the amount of fluid dispensed.

In using pipettes, two operations are often performed. First, the tip of the pipette is inserted into liquid and liquid is drawn in to the body cavity of the pipette through an opening or orifice. Second, the pipette is positioned over a second vessel and a measured amount of liquid released from the cavity. Liquid clinging to the outside of the tip from a first sample, can be transferred, as part of the second operation, into a next sample causing an error of too much liquid being dispensed. In the alternative, liquid which is intended to be released into a sample may cling to the tip causing too little fluid being dispensed.

Pipettes and pipette tips have been formed of plastics, including polystyrene. Although such plastics have been generally described as being hydrophobic, during the process of manufacturing, such hydrophobicity is often altered. For example, in rendering liquid dispensing devices sterile, such devices are generally irradiated. Irradiation generates charged groups and free radicals on the surface of the plastics and within the surrounding atmosphere. Gaseous molecules within the atmosphere such as ozone or free radical oxygen are highly reactive. Such free radicals and charged groups on the surface of the polystyrene, polyethlyene or polypropylene in the presence of the atmosphere, react in a manner which functionalizes the surface, altering its hydrophobicity.

In addition, in molding processes used in making devices of polystyrene, polyethlyene and polypropylene, lubricants are commonly used to facilitate removal of the device from the mold. Common mold lubricants include stearic acid and zinc stearate. Such mold lubricants are also oxidized during the irradiation process and become less hydrophobic.

There are a number of post molding treatments to render polymer surfaces hydrophobic such as silicone oils and various oils of hydrocarbon origin. The disadvantage is that oils migrate and dissolve in various solvents as well as adding contaminants to the fluid being contained within them. These surfaces are inherently unstable and can yield variable results. In addition, irradiation can alter their hydrophobicity and therefore their function.

Fluoropolymer lubricating agents have been used for both exterior and interior lubrication of polyolefin films during extrusion processes, for improving surface finish and for improving the melt rheology characteristics.

There are many articles of manufacture for which retention of liquids or aqueous soluble materials may be important. By way of example, the function of containment vessels; probes, such as temperature or flow sensors; solid supports for capturing molecules of interest; filters; membranes; and tubing for conveying liquids; may be influenced by carry over from one liquid sample to another. Such carry over may be a source of error or contamination.

BRIEF DESCRIPTION OF THE INVENTION

The present invention features hydrophobic molded articles of manufacture. One embodiment of the present invention features a hydrophobic molded article of manufacture comprising an inner matrix and an outer surface. The molded article has a composition comprising a mixture of a molded plastic and a fluoropolymer. The outer surface of the molded article is capable of being irradiated to form a sterilized molded article with a hydrophobic outer surface.

As used herein, the term "fluoropolymer" means a fluoridated copolymer capable of incorporation into plastics. Typical fluoridated copolymers comprise without limitation, vinylidene fluoride hexafluoropropene and polyvinylidene difluoride. Preferred fluoropolymer compositions are Viton® Free Flow marketed by Dupont Corporation, and Kynar-Flex® marketed by Penwalt Corporation. Compositions marketed under the Viton® Free Flow trademark are a mixture of vinylidene fluoride and hexafluoropropene copolymersN Compositions marketed under the Kynar-Flex® trademark are polyvinylidene difluoride. Viton® Free Flow products are sold as processing aids in the molding industry. The products are divided into series having special features for different applications. For example, series 10 products are sold as pellets, series 20 products are sold as powder blends, and series 30 is sold as a combination of polyolefin and fluoride copolymers for evaluation purposes. Each of the product series may also vary slightly in the use of excipients and other material to prevent gelling or massing. As used herein Viton® Free Flow and Kynar-Flex® mean such products sold by Penwalt Corporation and DuPont Corporation and similar products marketed by such companies and others under other trademarks.

Preferably, the fluoropolymer has a concentration gradient within the plastic in which the fluoropolymer has a higher concentration proximal to the outer surface with respect to the inner matrix.

As used herein, the term plastic is used in the sense of a material that contains as an essential ingredient an organic substance of large molecular weight, is solid in its finished state, and at some stage in its manufacture or its processing into finished articles can be shaped by flow. Plastics can be grouped in the following classifications comprising acrylics, cellulosics, epoxide, polyamides, polyesters, polyolefins, polystyrene, silicones, vinyl plastics, polycarbonates, polychloroethers and polymethylpentenes.

Preferably, the plastic is polystyrene. Preferably, the plastic and fluoropolymer are mixed in a ratio of between 50 to 2500 parts per million (ppm) fluoropolymer to plastic, and more preferably, approximately 100–1000 ppm fluoropolymer to plastic.

Two preferred compositions are 100 ppm vinylidene fluoride and hexafluoropropene in polystyrene and 100 ppm polyvinylidene difluoride in polystyrene. The compositions comprised of 100 ppm fluoropolymer to plastic are transparent and maintain hydrophobicity after irradiation. Irradiation is often used to sterilize plastic. High temperatures may alter the features of the article. As used herein, irradiation means bombardment with high energy particles or gamma rays.

The sterile hydrophobic molded articles of manufacture of the present invention are ideally suited for use as devices for dispensing, containing, piping, and probing liquids. Although the present invention should not be limited to a particular manner of operation, it is believed that the fluoropolymers are resistant to functionalization which functionalization normally occur in plastics upon irradiation.

One further embodiment of the present invention features a device for dispensing a fluid comprising a housing having an outer surface and an inner matrix. The housing has an opening defining an orifice adapted to receive and dispense a fluid. The housing is comprised of a mixture of a molded plastic and fluoropolymer. The fluoropolymer conveys a hydrophobic property to the outer surface. The hydrophobic property of the outer surface is maintained even after irradiation.

Preferably, the fluoropolymer has a concentration in the plastic in which the fluoropolymer has a higher concentration proximal to the outer surface with respect to the inner matrix.

Preferably, the plastic is a polystyrene. A preferred fluoropolymer is selected from the group of fluoropolymers comprising polyvinylidene difluoride, vinylidene fluoride and hexafluoropropene.

Preferably, the plastic and fluoropolymer are mixed in a ratio of 50 to 2500 ppm fluoropolymer to plastic, more preferably, approximately 100 to 1000 ppm fluoropolymer to plastic. Two most preferred compositions are 100 ppm vinylidene fluoride and hexafluoropropene in polystyrene and 100 ppm polyvinylidene difluoride in polystyrene.

Individuals skilled in the art will recognize that other compositions may be introduced into the plastic composite to impart other features. By way of example, without limitation, dyes or coloring agents may be used to alter the appearance of the plastic, and fibers may be used in the composite to impart tensile strength.

The device for dispensing a fluid may further comprise a containment vessel to hold the liquid to be dispensed. Typical pipettes include a cylindrical tube extending from the pipette tip forming a containment vessel in communication with the orifice. Preferably, the containment vessel is made from the hydrophobic material of the present invention such that liquids are not retained about the surfaces brought in contact with the fluid.

A further embodiment of present invention features a method of making a sterile hydrophobic article of manufacture. The method comprises the steps of combining plastic and a fluoropolymer to form a molded article having an inner matrix and an outer surface. The article is irradiated to form a sterile article which article retains hydrophobic properties.

Preferably, the fluoropolymer has a concentration gradient in the plastic in which the fluoropolymer has a higher concentration proximal to the outer surface with respect to the inner matrix.

Preferably, the fluoropolymer is selected from the group of fluoropolymers consisting of polyvinylidene difluoride, vinylidene fluoride and hexafluoropropene. Preferably, the plastic is selected from the group of plastics consisting of acrylics, cellulosics, epoxies, polyamides, polyesters, polyolefins, polystyrenes, silicones, vinyl plastics, polycarbonates and polychloroethers. A preferred plastic is polystyrene.

Preferably, the fluoropolymer has a concentration in the plastic of between 50 ppm to 2500 ppm. A preferred concentration range of fluoropolymer in the plastic is approximately 100 ppm to 1000 ppm. A most preferred concentration of fluoropolymer in the plastic is approximately 100 ppm.

Other features and advantages of the present invention will be apparent from the following description which, by way of illustration shows preferred embodiments of the present invention and the principles thereof and what is now considered to be the best mode to apply these principles.

DETAILED DESCRIPTION

The present invention is described in detail as a sterile hydrophobic molded article of manufacture, with the understanding that the present disclosure is to be considered an exemplification of the principles of invention and it is not intended to limit the invention to the embodiment illustrated. The present invention can be used wherever it is desirable to produce a sterile hydrophobic molded article. The embodiments of the present invention have particular application for dispensing fluids where accuracy is critical. Examples of applications of the present invention include pipettes, calibrated capillary tubes, conventional droppers and syringes. Embodiments of the present invention have applications in tubing for conveying liquids, containment vessels for holding liquids and probes for insertion in liquids where carryover from one sample to another may be important.

Figure 1:
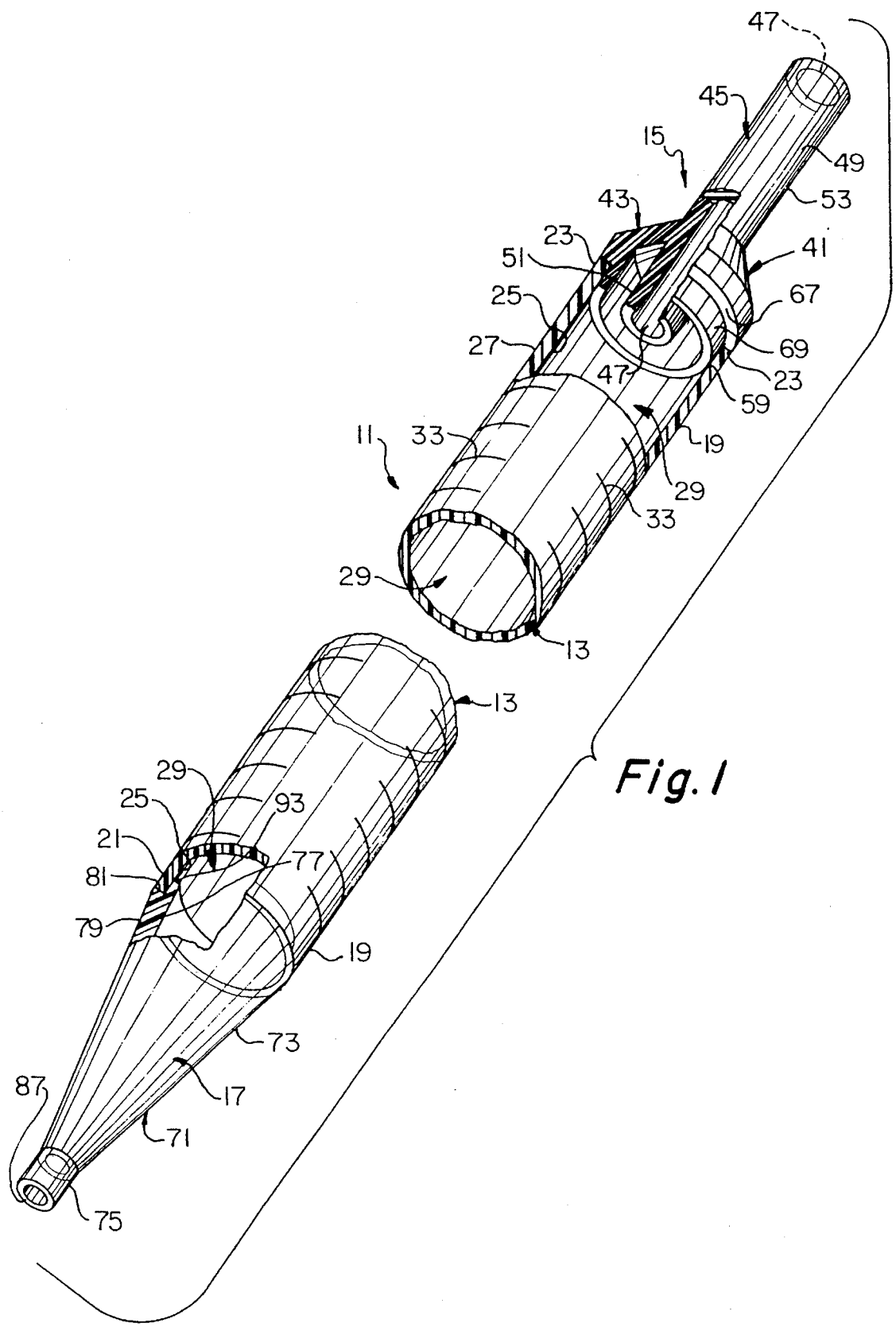
FIG. 1 is a side perspective view with partial cut-away of a dispensing device embodying features of the present invention.

A sterile hydrophobic molded article of manufacture in the form of a pipette, generally designated by the numeral 11, is illustrated in FIG. 1. The pipette 11 is comprised of a tube 13, an end piece 15 and a tip 17.

The pipette 11, as illustrated, has dimensions appropriate for a 50 ml capacity device with an overall length of approximate 27 cm and overall diameter of approximately 1.8 cm. Devices of other capacities can be readily sized by individuals skilled in the art.

The tube 13 has a cylindrical wall 19, having two ends 21 and 23, an inner surface 25 and an outer surface 27. One of the ends 21 is affixed to tip 17 and one of the ends 23 is affixed to end piece 15. The term "affixed" is used in a broad sense to mean attached to by adhesives, interfitting surfaces, plastic welding by chemicals or heat, bonding, and molded and shaped to be integral as a unitary structure, and the like.

The inner surface 25, in cooperation with inner surfaces of the tip 17 and end piece 15, which will be discussed later, defines a cylindrical chamber 29 capable of receiving and containing fluids. Preferably, the cylindrical wall 19 is transparent to allow operators to view the contents of the pipette 11. The outer surface 27 of the cylindrical wall 19 has measuring indicia 33, of which only a representative group of indicia are shown. Operators are able to compare the volume of fluid contained within cylindrical chamber 29 with measuring indicia 33 to determine fluid volumes.

Figure 2:
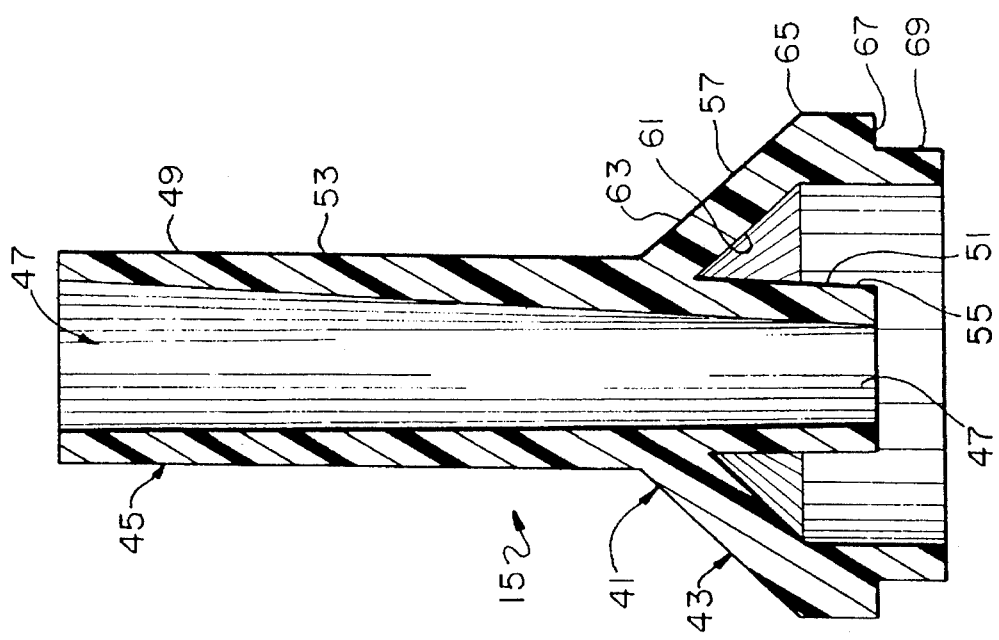
FIG. 2 is a side sectional view of the tip of the dispensing device of FIG. 1.

Turning now to FIG. 2, the end piece 15 of the pipette 11 is shown in greater detail. The end piece 15 is comprised of a housing 41 having a frustoconical section 43 and a conduit section 45. An opening 47 extends axially through the conduit section 45.

The conduit section 45 has two parts, an exterior extension 49 and an interior extension 51. The exterior extension 49 has a cylindrical wall 53 which extends from the frustoconical section 43. The exterior extension 49 is adapted to be received on vacuum and air pressure means for moving air in and out of the opening 51.

The interior extension is comprised of a cylindrical wall 55. The interior extension 51 and the opening 47 are slightly tapered in order to retain a cotton piece (not shown) which acts as a filter to retain liquid which could be carried into the vacuum source when liquid is pulled into the pipette, and allow sterile air to enter during dispensing.

The frustoconical section 43 has a conical wall 57. The conical wall 57 has an inner wall 61 and an outer wall 63. The outer wall has an outer edge 65 radially inwardly projecting upper wall 67 and an axially extending receiving wall 69. Receiving wall 69 is a cylindrical wall adapted to receive and interfit with the inner surface 25 of tube 19.

Turning now to FIGS. 1 and 2, the upper edge 23 of the tube 19 abuts against the upper wall 67 of the frustoconical section 43. The inner wall 61 of the frustoconical section 43 and the interior extension 51 defines the chamber 29 about the end piece 15.

Figure 3:
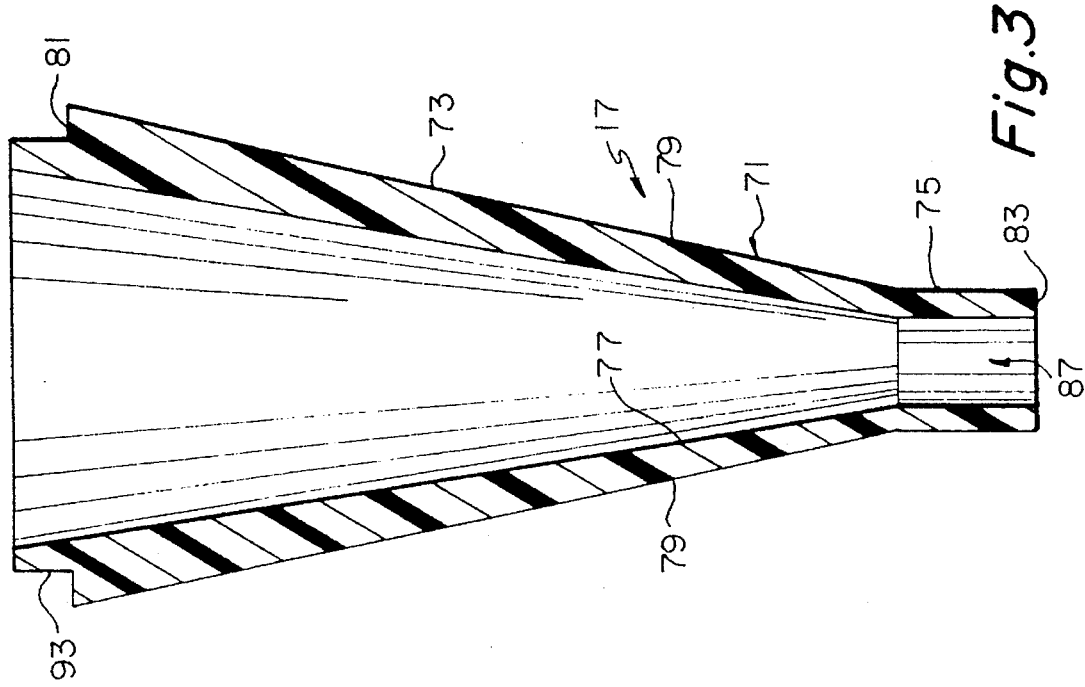
FIG. 3 is a side sectional of the end piece of the dispensing device of FIG. 1; and, FIG. 4 is a graph illustrating the performance of dispensing devices embodying features of the present invention.

Turning now to FIG. 3, the tip 17 has a tip housing 71 shaped as a funnel. Housing 71 has a frustoconical section 73 which tapers into a conduit section 75. Housing 71 has an inner wall 77, an outer wall 79, a top wall 81, and a bottom wall 83. Inner wall 77 and bottom wall 83 have an opening 87 extending through the conduit section 75 for conveying liquids. Inner wall 77 of tip 17, inner surface 25 of tube 13 and inner extension 51 and inner wall 61 of end piece 15, define chamber 29 for receiving and containing fluids.

Projecting upward from upper wall 81 is flange 93. Flange 93 is capable of being received within inner surface 25 of tube 13. End 21 of tube 13 abuts against upper wall 81. Inner surface 25 and flange 93 are joined in sealing engagement. Those skilled in the art will readily recognize, that tube 13, tip 17, and end piece 15 can be molded as a unitary structure.

Inner wall 77, outer wall 79, upper wall 81 and lower wall 83 define the surfaces of the tip housing 73. Tip housing 73 has a inner matrix extending from such surfaces to its interior.

Similarly, tube 13 has an inner matrix extending from inner surface 25, outer surface 27, and edges 21 and 23 to the interior. Similarly, the end piece 15 has an inner matrix extending inward from interior surface 61 and exterior surface 63.

The tube 13, and end piece housing 41, and tip housing 77 have a composition comprising a mixture of a molded plastic and a fluoropolymer. The fluoropolymer has a concentration gradient within the plastic in which the fluoropolymer has a higher concentration proximal to the outer surfaces with respect to the inner matrices of the tip housing 73, tube 13 and end piece housing 41.

The pipette 11 is irradiated to form a sterilized molded article. The fluoropolymer at the outer surface maintains the hydrophobic characteristics of the pipette 11 through the sterilization process. Tip 17 exhibits a contact angle for aqueous fluid of greater than 80° after irradiation. Most preferably, the tip 17 exhibits a contact angle for aqueous fluids of between 86° and 89°.

The plastic used in forming the inner matrix may comprise acrylics, cellulosics, epoxies, polyamides, polyesters, polyolefins, polystyrene, silicones, vinyl plastics, polycarbonates and polychloroethers.

Preferably, the plastic is polystyrene. The fluoropolymer is comprised of at least one fluoropolymer including polyvinylidene difluoride, vinylidene fluoride, and hexafluoropropene. A preferred fluoropolymer is Viton® Free Flow sold by DuPont Corporation and Kynar-Flex®, marketed by Penwalt Corporation.

In operation, conduit section 49 of end piece 15 is placed in communication with an air control assembly (not shown) for controlling the movement of air into chamber 29. Opening 87 of tip 17 is placed in communication with a liquid. Air is withdrawn through opening 47 of end piece 15, drawing fluid through opening 87 of tip 17.

As opening 87 is withdrawn from the liquid, liquid will not appreciably adhere to outer wall 79 or lower wall 83. In dispensing the liquid, the tip 13, having carried no liquid on outer wall 79 or lower wall 83, will not deliver more liquid than intended. Liquid dispensed from pipette 11 will not adhere to inner wall 77, outer wall 89, or lower wall 87, allowing the pipette tip 11 to dispense the intended volume.

In the event the entire volume of liquid in chamber 29 is emptied, inner wall 25 of tube 13 and inner wall 77 of tip 15, will not retain aqueous liquids. The hydrophobic surfaces repel water and droplets are less likely to be formed on the inner surfaces. The emptying of the pipette 11 is more complete.

EXAMPLE 1

Vinylidene fluoride-hexafluoropropene copolymers sold under the tradename Viton® Free Flow, were combined with a non-lubricated virgin polystyrene, at a concentration of 100 ppm fluoropolymer to polystyrene.

The combination was mixed in a twin screw extruder to form an extrusion product. The extrusion product was in a form of a ⅛" diameter rod which was air cooled and chipped for later use. The extrusion product in a concentration of 100 ppm was stable and clear.

EXAMPLE 2

Polyvinylidene difluoride marketed under the trademark Kynar-Flex®, was combined with polystyrene (Polysar® 101300) at concentrations of 2500 ppm, 1000 ppm, 100 ppm, 50 ppm of fluoropolymer to polystyrene and mixed in a twin screw extruder to form an extrusion products.

Composites having concentrations of 50 ppm and 100 ppm were clear and stable. The extrusion product was in a form of a ⅛" diameter rod, which was air cooled, and chipped up for later use. Composites having concentrations of 1000 ppm and 2500 ppm were stable and opaque.

EXAMPLE 3

Polystyrene-fluoropolymer composites having 100 ppm vinylidene fluoride-hexafluoropropene of the previous examples were utilized to form pipettes. Each composite was injected under conventional conditions for polystyrene into a mold to form pipette tips. Each pipette tip was irradiated with an electron beam and gamma radiation source and the contact angles were measured.

Similar pipette tips were formed with polystyrene using and zinc stearate as lubricant. The zinc stearate lubricated polystyrene tips were irradiated and the contact angle measured. The contact angles after sterilization are indicated for all tips in Table 1.

TABLE 1

| Sample | Contact Angle Measurement | | | | |
|---|---|---|---|---|---|
| | 1 | 2 | 3 | 4 | 5 |
| Polystyrene-vinylidene fluoride-hexafluoropropene | | | | | |
| 1 | 88 | 86 | 86 | 87 | |
| 2 | 86 | 87 | 87 | 88 | |
| 3 | 86 | 86 | 86 | 87 | |
| 4 | 89 | 88 | 87 | 86 | |
| Polystyrene-Zinc Stearate | | | | | |
| 1 | 70 | 69 | 71 | 70 | 69 |
| 2 | 71 | 70 | 70 | 71 | 70 |
| 3 | 70 | 71 | 71 | 70 | 69 |
| 4 | 70 | 68 | 69 | 70 | 70 |

The polystyrene-vitol pipette tips exhibited an average contact angle of 87° whereas the polystryrene-zinc stearate pipette tips exhibited an average contact angle of 69°.

The data suggests that the polyvinylidene difluoride-polystyrene composites and the vinylidene fluoride-hexafluoropropene-polystyrene composites are more hydrophobic than the polystyrene-zinc stearate composites before sterilization and after sterilization.

EXAMPLE 5

Tubes and end pieces were formed with the composites formed in Example 1 and Example 2 by extruding and molding the composites into appropriate shapes. The tubes, end pieces, and tips were assembled into pipettes.

Tubes and end pieces were also made with polystyrene lubricated with zinc stearate. The tubes, end pieces and tips were assembled into pipettes.

EXAMPLE 6

Pipettes of different concentrations of fluoropolymer and polystyrene were subjected to irradiation and evaluated. Each pipette was filled with 50 ml of aqueous medium which was aliquotted at 10 ml per COSTAR Catalog #3055 flask to a total of five flasks. The test utilized movement of the pipette from flask to flask in both horizontal and vertical directions. The test involved the dispensing of aliquots which allows the air pressure above the fluid to vary.

The procedure was performed in a laminar flow hood using sterile technique. The pipettes were challenged by the rigors of tissue culture technique. Tissue culture technique required the removal of flask caps to dispense an aliquot and replacement of the cap following the actions. Tests were performed on 115 sterile pipettes. Of the 115 pipettes, nine pipettes were controls comprised of virgin polystyrene. The remaining 106 pipettes were comprised of polyvinylidene difluoride-polystyrene (PDP) or vinylidene fluoride-hexafluoropropene polystyrene (VHP). The total drips from each pipette was noted and average drips per piece were calculated. The results are set forth below in Table 2.

TABLE 2

| Material | | Pieces Tested | Average Drips/Piece | Total Drips | Tip Color |
|---|---|---|---|---|---|
| *VHP | 1000 ppm | 10 | 0 | 0 | opaque |
| VHP | 100 ppm | 23 | 0.04 | 1 | clear |
| VHP | 50 ppm | 22 | 0.3 | 6 | clear |
| *PDP | 2500 ppm | 10 | 0 | 0 | opaque |
| *PDP | 1000 ppm | 10 | 0.1 | 1 | opaque |
| PDP | 100 ppm | 21 | 0.1 | 1 | opaque |
| **PDP | 50 ppm | 10 | 0.8 | 8 | clear |
| Controls | | 9 | 0.8 | 8 | clear |

The tests marked with an asterisk involved only 10 pieces.

Figure 4:
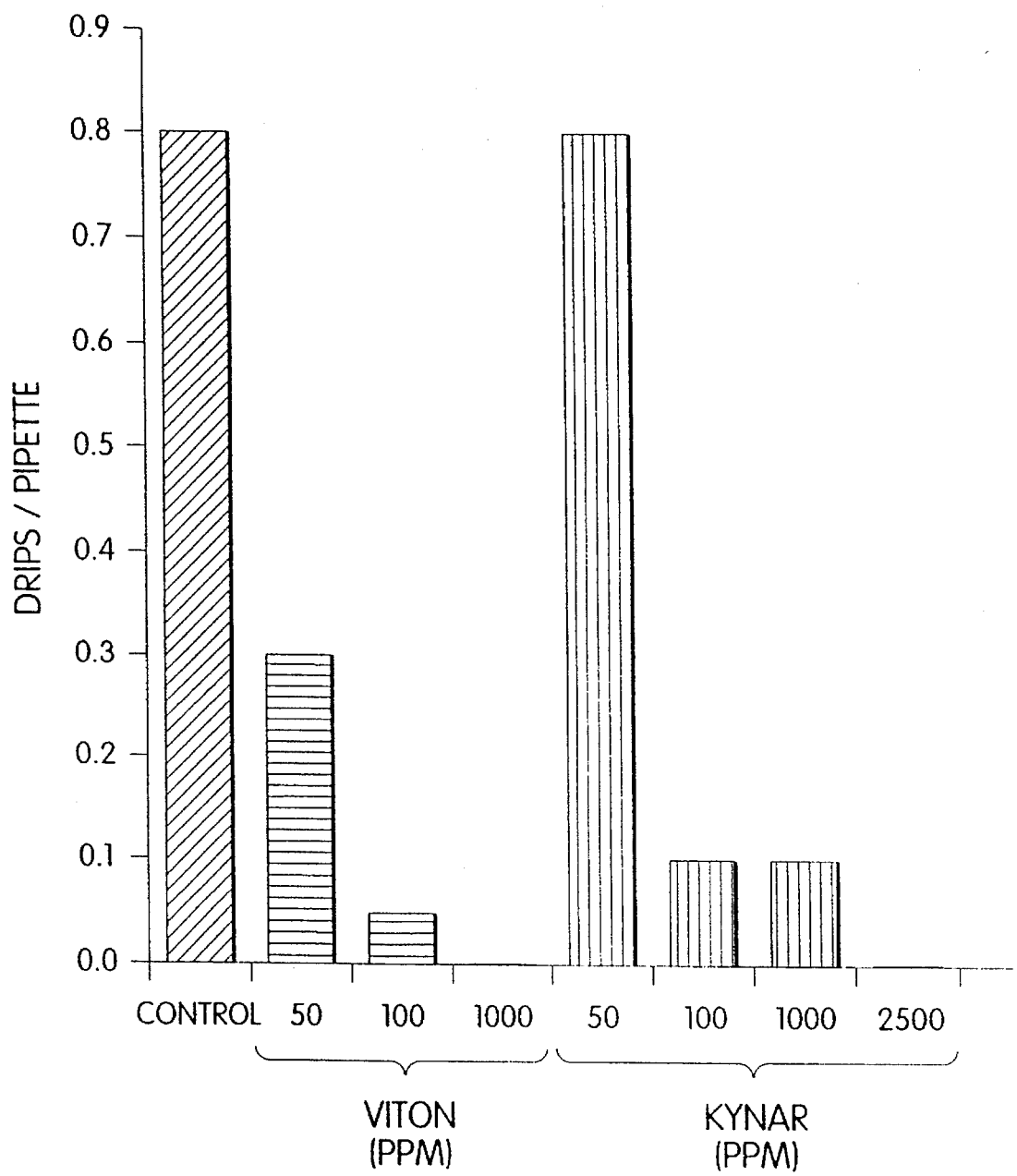

These data are summarized in FIG. 4. FIG. 4 depicts the various concentrations of fluoropolymer composites in comparison with controls.

A preferred composition comprises vinylidene fluoride and hexafluoropropene in polystyrene in a concentration of 50–1000 ppm fluoropolymer. A most preferred concentration comprises approximately 100 ppm, 1000 ppm vinylidene fluoride and hexafluoropropene in polystyrene and most preferably approximately 100 ppm vinylidene fluoride and hexafluoropropene in polystyrene. At 100 ppm vinylidene fluoride-hexafluoropropene in polystyrene, composites maintained their clear nature and have a significant reduction in number of drips.

A preferred polyvinylidene difluoride in polystyrene composition is comprised of between 100–2500 ppm fluoropolymer. Most preferably, a concentration of approximately 100–1000 ppm polyvinylidene difluoride, and preferably within the lower range of approximately 100 ppm polyvinylidene difluoride. The preferred range of fluoropolymers feature a clear plastic composite to allow operators to control the dispensing of fluids more readily. However, in mechanical dispensing devices, the opaque nature of plastics having a high concentration of fluoropolymer may not be significant.

Applicants have presented methods and apparatus for making and using a sterile, hydrophobic molded article of manufacture. Such sterile, hydrophobic articles of manufacture are useful in the fluid dispensing devices such as pipette tips, curvettes, capillary tubes, syringes, tubing, and vessels, and other articles which require contact with aqueous fluid such as probes for insertion into fluids and the like.

Thus, while preferred embodiments of the invention have been described, the present invention is capable of variation and modification and therefore, the present invention should not be limited to the precise details set forth, but should include such changes and alterations as fall within the purview of the following claims.

What is claimed is:

1. A sterile article of manufacture for dispensing a liquid comprising a housing having an opening for dispensing a liquid, said housing is molded from a mixture of polystyrene and a fluoropolymer and sterilized by irradiation, said fluoropolymer selected from the group of fluoropolymers consisting of polyvinylidene difluoride, vinylindene fluoride and hexafluoropropene having a concentration of 100 to 2,500 parts per million fluoropolymer in polystyrene, said concentration being effective to maintain a hydrophobic outer surface after irradiation, and said housing exhibiting a contact angle for aqueous fluid of greater than 80° following sterilization radiation of the outer surface of the housing.

2. The article of claim 1 wherein said article of manufacture is a pipette tip.

* * * * *